US012793854B2

(12) United States Patent
Rokach et al.

(10) Patent No.: US 12,793,854 B2
(45) Date of Patent: Nov. 10, 2026

(54) SYSTEM AND METHOD OF PREDICTING EFFICACY OF TREATMENT

(71) Applicant: B. G. NEGEV TECHNOLOGIES AND APPLICATIONS LTD., Beer-Sheva (IL)

(72) Inventors: Lior Rokach, Beer Sheva (IL); Bracha Shapira, Beer Sheva (IL); Shimon Ben-Shabat, Beer Sheva (IL); Guy Shtar, Beer Sheva (IL); Adi Jabarin, Beer Sheva (IL); Eyal Mazuz, Beer Sheva (IL)

(73) Assignee: B. G. NEGEV TECHNOLOGIES AND APPLICATIONS LTD., Beer-Sheva (IL)

( * ) Notice: Subject to any disclaimer, the term of this patent is extended or adjusted under 35 U.S.C. 154(b) by 0 days.

(21) Appl. No.: 18/870,063

(22) PCT Filed: May 29, 2023

(86) PCT No.: PCT/IL2023/050547
§ 371 (c)(1),
(2) Date: Nov. 27, 2024

(87) PCT Pub. No.: WO2023/233396
PCT Pub. Date: Dec. 7, 2023

(65) Prior Publication Data

US 2025/0329457 A1 Oct. 23, 2025

Related U.S. Application Data

(60) Provisional application No. 63/430,473, filed on Dec. 6, 2022, provisional application No. 63/404,251, filed
(Continued)

(51) Int. Cl.
*G16H 50/20* (2018.01)
*G16H 20/10* (2018.01)
*G16H 70/40* (2018.01)

(52) U.S. Cl.
CPC ............ *G16H 50/20* (2018.01); *G16H 20/10* (2018.01); *G16H 70/40* (2018.01)

(58) Field of Classification Search
None
See application file for complete search history.

(56) References Cited

U.S. PATENT DOCUMENTS

2020/0365270 A1 11/2020 Kazemi Oskooei et al.
2021/0065913 A1* 3/2021 Yuan ........................ G06N 3/08
(Continued)

FOREIGN PATENT DOCUMENTS

| | | | |
|---|---|---|---|
| CN | 112435720 | A | 3/2021 |
| CN | 114334038 | A | 4/2022 |
| WO | 2018075767 | A1 | 4/2018 |

OTHER PUBLICATIONS

Celebi et al. ("Evaluation of knowledge graph embedding approaches for drug-drug interaction prediction in realistic settings." BMC bioinformatics 20.1 (2019): 726) (Year: 2019).*
(Continued)

*Primary Examiner* — Christopher B Tokarczyk
(74) *Attorney, Agent, or Firm* — The Roy Gross Law Firm, LLC; Roy D. Gross

(57) ABSTRACT

A system and method of predicting efficacy of treatment of a predetermined medical condition by at least one processor may include obtaining a Drug-Drug Interaction (DDI) embedding value, representing occurrence of DDIs between a substance of interest and one or more drugs selected from a plurality of baseline drugs, in a DDI embedding space; receiving a chemical structure data element, representing a chemical structure of the substance of interest; and predict-
(Continued)

ing efficacy of the substance of interest in treatment of the predetermined medical condition based on (i) the DDI embedding value and (ii) the structure data element.

18 Claims, 6 Drawing Sheets

Related U.S. Application Data on Sep. 7, 2022, provisional application No. 63/346, 868, filed on May 29, 2022.

(56) References Cited

U.S. PATENT DOCUMENTS

| | | | | |
|---|---|---|---|---|
| 2022/0101972 | A1* | 3/2022 | Bajpai | G16H 70/40 |
| 2022/0358373 | A1* | 11/2022 | Bucher | G06N 3/045 |
| 2023/0067528 | A1* | 3/2023 | Guo | G06N 3/0895 |
| 2023/0230662 | A1* | 7/2023 | Sarshogh | G06N 3/0895 706/12 |

OTHER PUBLICATIONS

Stokes JM, Yang K, Swanson K, Jin W, Cubillos-Ruiz A, Donghia NM, MacNair CR, French S, Carfrae LA, Bloom-Ackermann Z, Tran VM, Chiappino-Pepe A, Badran AH, Andrews IW, Chory EJ, Church GM, Brown ED, Jaakkola TS, Barzilay R, Collins Jj. A Deep Learning Approach to Antibiotic Discovery. Cell. Feb. 20, 2020;180(4):688-702.e13. doi: 10.1016/j.cell.2020.01.021. Erratum in: Cell. Apr. 16, 2020;181(2):475-483. doi: 10.1016/j.cell.2020.04.001. PMID: 32084340; PMCID: PMC8349178.

Ojima I. Use of fluorine in the medicinal chemistry and chemical biology of bioactive compounds—a case study on fluorinated taxane anticancer agents. Chembiochem. May 3, 2004;5(5):628-35. doi: 10.1002/cbic.200300844. PMID: 15122634.

Ramachandran S, Srivastava SK. Repurposing Pimavanserin, an Anti-Parkinson Drug for Pancreatic Cancer Therapy. Mol Ther Oncolytics. Sep. 2, 2020;19:19-32. doi: 10.1016/j.omto.2020.08.019. PMID: 33024816; PMCID: PMC7527685.

Tanoli Z, Vaha-Koskela M, Aittokallio T. Artificial intelligence, machine learning, and drug repurposing in cancer. Expert Opin Drug Discov. Sep. 2021;16(9):977-989. doi: 10.1080/17460441.2021.1883585. Epub Feb. 12, 2021. PMID: 33543671.

Celebi, R., Uyar, H., Yasar, E. et al. Evaluation of knowledge graph embedding approaches for drug-drug interaction prediction in realistic settings. BMC Bioinformatics 20, 726 (2019). https://doi.org/10.1186/s12859-019-3284-5.

PCT International Search Report and Written Opinion for International Application No. PCT/IL2023/050547, mailed Oct. 17, 2023, 9pp.

Kounatidis, Dimitris et al., "Third-Generation Tetracyclines: Current Knowledge and Therapeutic Potential", Biomolecules, vol. 14, No. 7, Jun. 30, 2024 (Jun. 30, 2024), p. 783, XP093389121, CH, ISSN: 2218-273X, DOI: 10.3390/biom14070783, 28 pp. Retrieved from the Internet: [https://www.mdpi.com/2218-273X/14/7/783/pdf?version=1719731900].

Jabarin, Adi et al., "Eravacycline, an antibacterial drug, repurposed for pancreatic cancer therapy: insights from a molecular-based deep learning model", Briefings in Bioformatics, vol. 25, No. 3, Mar. 27, 2024 (Mar. 27, 2024), XP093389118, GB, ISSN: 1467-5463, 8pp. DOI: 10.1093/bibbbae108 Available online: [https://academic.oup.com/bib/article-abstract/25/3/bbae108/7655596].

Rebecca Lamb et al., "Antibiotics that target mitochondria effectively eradicate cancer stem cells, across multiple tumor types: Treating cancer like an infectious disease", ONCOTARGET, vol. 6, No. 7, Mar. 10, 2015 (Mar. 10, 2015), pp. 4569-4584, XP055405961, DOI: 10.18632/oncotarget.3174.

Quinn, Bridget A. et al., "Pancreatic Cancer Combination Therapy Using a BH3 Mimetic and a Synthetic Tetracycline", AACR Annual Meeting 2019, vol. 75, No. 11, May 31, 2015 (May 31, 2015), pp. 2305-2315, XP093389134, ISSN: 0008-5472, DOI: 10.1158/0008-5472.can-14-3013, Retrieved from the Internet: URL:https://aacrjournals.org/cancerres/article-abstract/75/11/2305/599825>.

Bin Zhou et al., "Drug Repurposing Based on Drug-Drug Interaction", Chemical Biology & Drug Design Blackwell Munksgaard, Hoboken, USA, vol. 85, No. 2, Jul. 2, 2014 (Jul. 2, 2014), pp. 137-144, XP072380590, ISSN: 1747-0277, DOI: 10.1111/CBDD.12378.

Zeng, Xiangxiang et al., "deepDR: a network-based deep learning approach to in silico drug repositioning", BIOINFORMATICS, vol. 35, No. 24, May 22, 2019 (May 22, 2019), pp. 5191-5198, XP093393993, GB, ISSN: 1367-4803, DOI: 10.1903/bioinformatics/btz418.

Deng, Yuanyuan et al., "A multi-task graph convolutional network modeling of drug-drug interactions and synergistic efficacy", 2021 IEEE International Conference on Bioinformatics and Biomedicine (BIBM), IEEE, Dec. 9, 2021 (Dec. 9, 2021), pp. 368-371, XP034066534, DOI: 10.1109/BIBM52615.2021.9669575.

Remzi Celebi et al., "Evaluation of knowledge graph embedding approaches for drug-drug interaction prediction in realistic settins", BMC Bioinforamtics, vol. 20, No. 1, Dec. 1, 2019 (Dec. 1, 2019), XP055727536, 14pp. DOI: 10.1186/s12859-019-3284-5.

Pengyong Li et al., "Learn molecular representations from large-scale unlabeled molecules for drug discover", arXiv.org, Cornell University Library, 201 Olin Library, Cornell University, Ithaca, NY, 14853, Dec. 21, 2020. arXiv:2012.11175, 20pp.

* cited by examiner

| Features | AUC (Anti-cancer activity prediction) |
| --- | --- |
| Molecular structure (e.g., "Smiles") | 0.806 |
| Molecular structure + DTI | 0.853 |
| Molecular structure + DDI | 0.897 |
| Molecular structure + DDI + DTI | 0.909 |

FIG. 4

SYSTEM AND METHOD OF PREDICTING EFFICACY OF TREATMENT

CROSS-REFERENCE TO RELATED APPLICATIONS

This application is a National Phase Application of PCT International Application No. PCT/IL2023/050547, having International Filing Date of May 29, 2023, Titled: "SYSTEM AND METHOD OF PREDICTING EFFICACY OF TREATMENT", which claims the benefit of priority of U.S. Patent Application No. 63/346,868, filed May 29, 2022 and U.S. Patent Application No. 63/404,251, filed Sep. 7, 2022 both titled "IDENTIFICATION AND CHARACTERIZATION OF DRUGS WITH NOVEL ANTI-CANCER ACTIVITY, SELECTED BY COMPUTATIONAL DRUG REPURPOSING STUDY, USING ARTIFICIAL INTELLIGENCE (AI) DEEP LEARNING MODELS", and U.S. Patent Application No. 63/430,473, filed Dec. 6, 2022 titled "SYSTEM AND METHOD OF PREDICTING EFFICACY OF TREATMENT", which are all hereby incorporated by reference in their entirety.

FIELD OF THE INVENTION

The present invention relates generally to the field of in-silicon simulation of biochemical processes. More specifically, these present invention relates to systems and methods of predicting efficacy of drug treatment to a predefined medical condition.

BACKGROUND OF THE INVENTION

As drug databases have grown, machine learning (ML) based approaches for determining drug efficacy in treatment of various malignancies have emerged. Such approaches identify new drug-disease interactions and may be used, for example to change a designation of an approved drug.

Currently available methods typically rely on similarity of chemical structure data between a baseline drug and a substance of interest, to predict an effect of the substance of interest on a biochemical target. Currently available methods may also make use of known datasets of Drug-Target interactions (DTIs), to predict an effect of the substance of interest on the biochemical target. Such methods subsequently analyze the predicted effect to gain an understanding regarding efficacy of treatment of a disease.

SUMMARY OF THE INVENTION

It may be appreciated that an additional step of analyzing a predicted effect of a substance of interest on the biochemical target, to determine efficacy of treatment of a disease, as currently performed in the art is (a) error prone, and (b) dependent upon the individual understanding of the underlying biochemical target and disease, and is therefore non-scalable.

As explained herein, embodiments of the invention may circumvent such disadvantage: By utilizing available data, regarding approval of baseline drugs by proper authorities (e.g., the FDA) for treatment of a first disease, embodiments of the invention may identify, predict or highlight efficacy of drugs or substances of interest, for treating a second disease (e.g., rather than predicting an effect on an interim biochemical target).

Additionally, embodiments of the invention may utilize available Drug-Drug Interaction data, to extract latent information, thereby improving prediction of drug efficacy.

Embodiments of the invention may include a method of predicting efficacy of treatment of a predetermined medical condition by at least one processor.

According to some embodiments, the at least one processor may obtain a Drug-Drug Interaction (DDI) embedding value, representing occurrence of DDIs between a substance of interest and one or more drugs selected from a plurality of baseline drugs, in a DDI embedding space; receive a chemical structure data element, representing a chemical structure of the substance of interest; and predict efficacy of the substance of interest in treatment of the predetermined medical condition based on (i) the DDI embedding value and (ii) the structure data element.

According to some embodiments, the at least one processor may predict efficacy of the substance of interest by: applying a first pretrained machine-learning (ML)-based model on (i) the DDI embedding value, and (ii) the structure data element; and providing an output of the first ML model as the prediction of efficacy of the substance of interest in treatment of the predetermined medical condition.

According to some embodiments, the at least one processor may obtain a Drug-Target Interaction (DTI) embedding value, representing occurrence of DTIs between the substance of interest and one or more biochemical targets selected from a plurality of biochemical targets, in a DTI embedding space; and predict efficacy of the substance of interest in treatment of the predetermined medical condition further based on the DTI embedding value.

According to some embodiments, the at least one processor may predict efficacy of the substance of interest by applying a first pretrained ML-based model on (i) the DDI embedding value, (ii) the structure data element, and (iii) the DTI embedding value; and providing an output of the first ML model as the prediction of efficacy of the substance of interest in treatment of the predetermined medical condition.

According to some embodiments, the chemical structure data element may be a line-notation description of the substance of interest.

According to some embodiments, the at least one processor may obtain a DDI embedding value by receiving a DDI data structure may include a plurality of entries, wherein each entry (i,j) represents a known DDI between a first substance (i) and a second substance (j) of a plurality of substances. The plurality of substances may include the plurality of baseline drugs and the substance of interest. The at least one processor may subsequently apply an embedding function on the DDI data structure, to extract a DDI embedding vector, representing known DDIs between the substance of interest and other baseline drugs of the plurality of baseline drugs, in the DDI embedding space; and calculate the DDI embedding value of the substance of interest based on the DDI embedding vector.

Additionally, or alternatively, the at least one processor may obtain a DTI embedding value by receiving a DTI data structure may include a plurality of entries, wherein each entry (i,j) represents a known DTI between a specific substance (i) of a plurality of substances and a specific biochemical target (j) of a plurality of biochemical targets. The plurality of substances may include the plurality of baseline drugs and the substance of interest. The at least one processor may subsequently apply an embedding function on the DTI data structure, to extract a DTI embedding vector, representing known DTIs between the substance of interest and the plurality of biochemical targets, in the DTI embedding space; and calculate the DTI embedding value of the substance of interest based on the DTI embedding vector.

According to some embodiments, the at least one processor may train the first ML based model by receiving a training dataset pertaining to one or more first baseline drugs; receiving one or more label data elements, pertaining to the one or more first baseline drugs, wherein each label annotates whether the respective baseline drug is approved for use as a remedy for the predetermined medical condition, or not; and using the one or more label data elements as supervisory data, to train the first ML based model, to predict efficacy of a target substance of interest in treatment of the predetermined medical condition.

Additionally, or alternatively, the at least one processor may train the first ML based model by receiving a training dataset that includes (i) one or more first DDI embedding values, corresponding to one or more respective, first baseline drugs, and (ii) one or more first structure data elements, corresponding to the one or more respective, first baseline drugs; receiving one or more label data elements, corresponding to the one or more respective, first baseline drugs, wherein each label annotates whether the respective baseline drug is approved for use as a remedy for the predetermined medical condition, or not; and using the one or more label data elements as supervisory data, to train the first ML based model, to predict efficacy of the one or more first baseline drugs in treatment of the predetermined medical condition, based on the one or more first DDI embedding values and one or more first structure data elements.

Additionally, or alternatively, the at least one processor may be configured to, during an inference stage, receive a second DDI embedding value and a second structure data element, corresponding to a target substance of interest; and predict efficacy of treatment of that target substance of interest, according to the second DDI embedding value and second structure data element, based on said training.

Additionally, or alternatively, the at least one processor may train the first ML based model by receiving a training dataset may include: (i) one or more first DDI embedding values, corresponding to one or more respective, first baseline drugs, (ii) one or more first DTI embedding values, corresponding to the one or more respective, first baseline drugs, and (iii) one or more first structure data elements, corresponding to the one or more respective, first baseline drugs; receiving one or more label data elements, corresponding to the one or more respective, first baseline drugs, wherein each label annotates whether the respective baseline drug is approved for use as a remedy for the predetermined medical condition, or not; and using the one or more label data elements as supervisory data, to train the first ML based model, to predict efficacy of the one or more first baseline drugs in treatment of the predetermined medical condition, based on the one or more first DDI embedding values, the one or more first DTI embedding values, and one or more first structure data elements.

Additionally, or alternatively, the at least one processor may be configured to, during an inference stage, receive a second DDI embedding value, a second DTI embedding value, and a second structure data element, corresponding to a target substance of interest; and predict efficacy of treatment of that target substance of interest, according to the second DDI embedding value, second DTI embedding value and second structure data element, based on said training.

Embodiments of the invention may include a system for predicting efficacy of treatment of a predetermined medical condition. Embodiments of the system may include a non-transitory memory device, wherein modules of instruction code are stored, and at least one processor associated with the memory device, and configured to execute the modules of instruction code.

Upon execution of said modules of instruction code, the at least one processor may be configured to obtain a Drug-Drug Interaction (DDI) embedding value, representing occurrence of DDIs between a substance of interest and one or more drugs selected from a plurality of baseline drugs, in a DDI embedding space; receive a chemical structure data element, representing a chemical structure of the substance of interest; and predict efficacy of the substance of interest in treatment of the predetermined medical condition based on (i) the DDI embedding value of the substance of interest and (ii) the structure data element of the substance of interest.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 4 is a table elaborating a comparison between different methods of drug treatment efficacy prediction.

Figure 1:
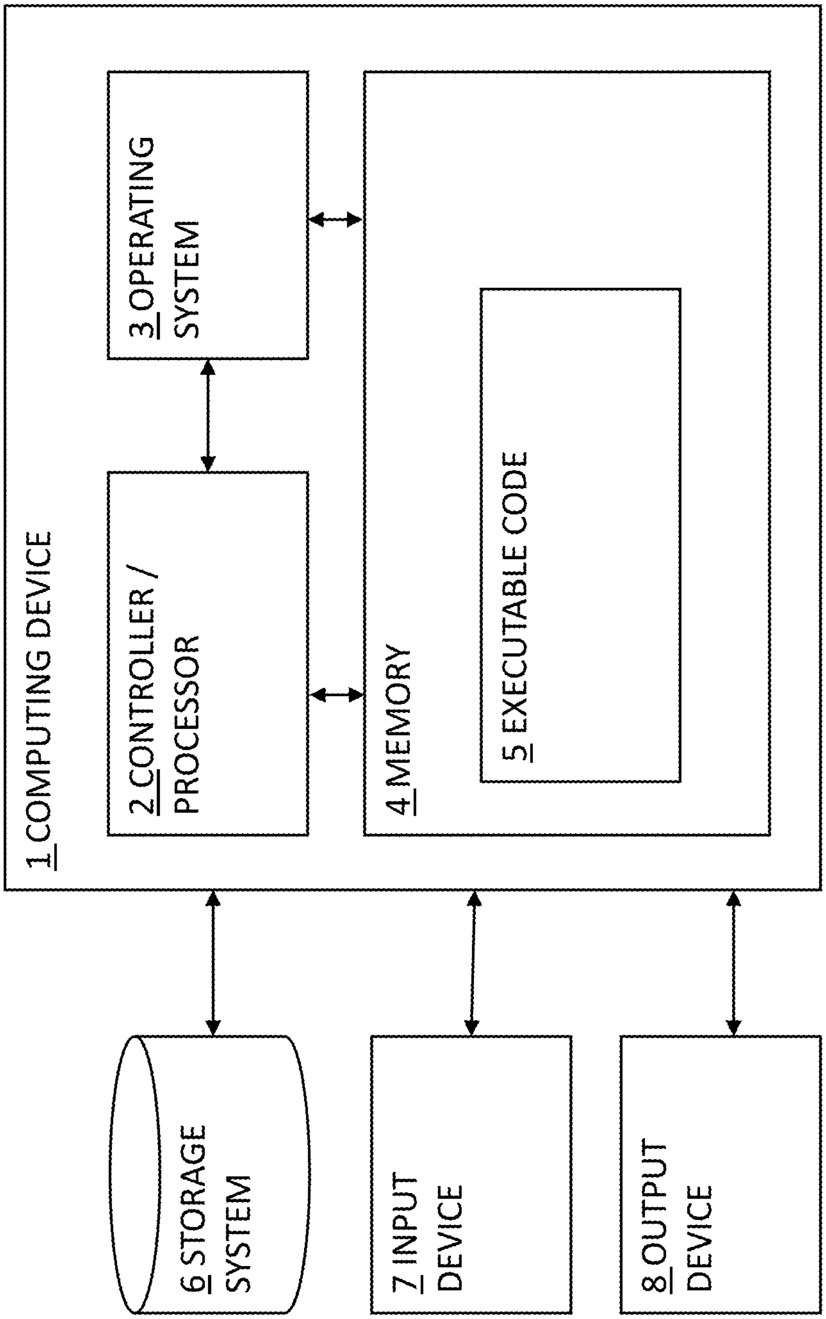
FIG. 1 is a block diagram, depicting a computing device which may be included in a system for predicting efficacy of drug treatment, according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, “processing,” “computing,” “calculating,” “determining,” “establishing”, “analyzing”, “checking”, or the like, may refer to operation(s) and/or process(es) of a computer, a computing platform, a computing system, or other electronic computing device, that manipulates and/or transforms data represented as physical (e.g., electronic) quantities within the computer’s registers and/or memories into other data similarly represented as physical quantities within the computer’s registers and/or memories or other information non-transitory storage medium that may store instructions to perform operations and/or processes.

Although embodiments of the invention are not limited in this regard, the terms “plurality” and “a plurality” as used herein may include, for example, “multiple” or “two or more”. The terms “plurality” or “a plurality” may be used throughout the specification to describe two or more components, devices, elements, units, parameters, or the like. The term “set” when used herein may include one or more items.

Unless explicitly stated, the method embodiments described herein are not constrained to a particular order or sequence. Additionally, some of the described method embodiments or elements thereof can occur or be performed simultaneously, at the same point in time, or concurrently.

Reference is now made to FIG. 1, which is a block diagram depicting a computing device, which may be included within an embodiment of a system for predicting efficacy of drug treatment, according to some embodiments.

Computing device 1 may include a processor or controller 2 that may be, for example, a central processing unit (CPU) processor, a chip or any suitable computing or computational device, an operating system 3, a memory 4, executable code 5, a storage system 6, input devices 7 and output devices 8. Processor 2 (or one or more controllers or processors, possibly across multiple units or devices) may be configured to carry out methods described herein, and/or to execute or act as the various modules, units, etc. More than one computing device 1 may be included in, and one or more computing devices 1 may act as the components of, a system according to embodiments of the invention.

Operating system 3 may be or may include any code segment (e.g., one similar to executable code 5 described herein) designed and/or configured to perform tasks involving coordination, scheduling, arbitration, supervising, controlling or otherwise managing operation of computing device 1, for example, scheduling execution of software programs or tasks or enabling software programs or other modules or units to communicate. Operating system 3 may be a commercial operating system. It will be noted that an operating system 3 may be an optional component, e.g., in some embodiments, a system may include a computing device that does not require or include an operating system 3.

Memory 4 may be or may include, for example, a Random-Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 4 may be or may include a plurality of possibly different memory units. Memory 4 may be a computer or processor non-transitory readable medium, or a computer non-transitory storage medium, e.g., a RAM. In one embodiment, a non-transitory storage medium such as memory 4, a hard disk drive, another storage device, etc. may store instructions or code which when executed by a processor may cause the processor to carry out methods as described herein.

Executable code 5 may be any executable code, e.g., an application, a program, a process, task, or script. Executable code 5 may be executed by processor or controller 2 possibly under control of operating system 3. For example, executable code 5 may be an application that may predict efficacy of drug treatment as further described herein. Although, for the sake of clarity, a single item of executable code 5 is shown in FIG. 1, a system according to some embodiments of the invention may include a plurality of executable code segments similar to executable code 5 that may be loaded into memory 4 and cause processor 2 to carry out methods described herein.

Storage system 6 may be or may include, for example, a flash memory as known in the art, a memory that is internal to, or embedded in, a micro controller or chip as known in the art, a hard disk drive, a CD-Recordable (CD-R) drive, a Blu-ray disk (BD), a universal serial bus (USB) device or other suitable removable and/or fixed storage unit. Data pertaining to specific drugs or substances may be stored in storage system 6 and may be loaded from storage system 6 into memory 4 where it may be processed by processor or controller 2. In some embodiments, some of the components shown in FIG. 1 may be omitted. For example, memory 4 may be a non-volatile memory having the storage capacity of storage system 6. Accordingly, although shown as a separate component, storage system 6 may be embedded or included in memory 4.

Input devices 7 may be or may include any suitable input devices, components, or systems, e.g., a detachable keyboard or keypad, a mouse and the like. Output devices 8 may include one or more (possibly detachable) displays or monitors, speakers and/or any other suitable output devices. Any applicable input/output (I/O) devices may be connected to Computing device 1 as shown by blocks 7 and 8. For example, a wired or wireless network interface card (NIC), a universal serial bus (USB) device or external hard drive may be included in input devices 7 and/or output devices 8. It will be recognized that any suitable number of input devices 7 and output device 8 may be operatively connected to Computing device 1 as shown by blocks 7 and 8.

A system according to some embodiments of the invention may include components such as, but not limited to, a plurality of central processing units (CPU) or any other suitable multi-purpose or specific processors or controllers (e.g., similar to element 2), a plurality of input units, a plurality of output units, a plurality of memory units, and a plurality of storage units.

The term neural network (NN) or artificial neural network (ANN), e.g., a neural network implementing a machine learning (ML) or artificial intelligence (AI) function, may be used herein to refer to an information processing paradigm that may include nodes, referred to as neurons, organized into layers, with links between the neurons. The links may transfer signals between neurons and may be associated with weights. A NN may be configured or trained for a specific task, e.g., pattern recognition or classification. Training a NN for the specific task may involve adjusting these weights based on examples. Each neuron of an intermediate or last layer may receive an input signal, e.g., a weighted sum of output signals from other neurons, and may process the input signal using a linear or nonlinear function (e.g., an activation function). The results of the input and intermediate layers may be transferred to other neurons and the results of the output layer may be provided as the output of the NN. Typically, the neurons and links within a NN are represented by mathematical constructs, such as activation functions and matrices of data elements and weights. At least one processor (e.g., processor 2 of FIG. 1) such as one or more CPUs or graphics processing units (GPUs), or a dedicated hardware device may perform the relevant calculations.

Figure 2A:
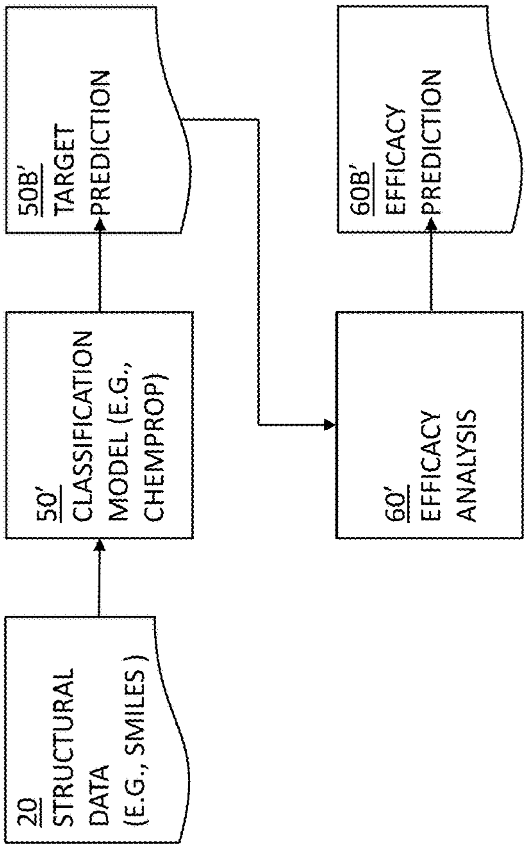
FIGS. 2A and 2B are schematic block diagrams depicting functionality of currently available systems for prediction of drug treatment efficacy, as known in the art.
Figure 2B:
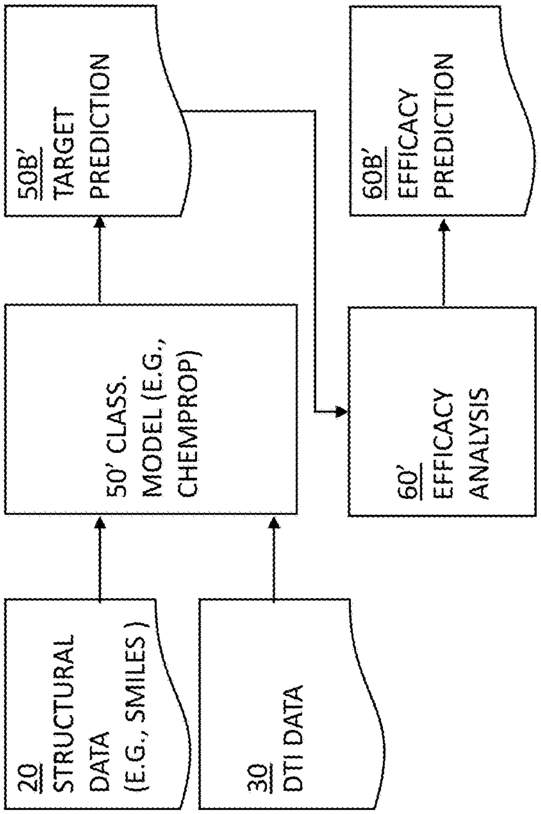

FIGS. 2A and 2B are schematic block diagrams depicting functionality of currently available systems for prediction of drug treatment efficacy, as known in the art. In both FIGS. 2A and 2B, an ML-based classification model 50' is trained to predict an effect of a substance of interest on a biochemical target 50B'. Such biochemical target 50B' may include, for example target molecules that are involved in pathogenesis of a predetermined medical condition, a biochemical pathway or process involved in this pathogenesis, and the like. The effect of a drug of interest on the biochemical target 50B' is then analyzed 60' to gain insight regarding efficacy in treatment of a specific malignancy 60B'. For example, a change in quantity or concentration of a biochemical target 50B', induced by a specific substance of interest may be empirically associated to specific phenotypes, and so an efficacy of the substance of interest in treatment of a specific malignancy 60B' may be evaluated.

The difference between FIGS. 2A and 2B lies in the type of drug-representative information presented to ML model 50' for prediction:

As shown in FIG. 2A, a common methodology includes training ML module to predict effect of a substance of interest on a specific target based on chemical, or molecular structural data 20. Such chemical structure data 20 may include a line-notation description of a drug or substance of interest. An example of a format of line-notation description includes the currently available Simplified Molecular-Input Line-Entry System (SMILES).

The motivation behind the methodology depicted in FIG. 2A is that substances or drugs of similar structure may exhibit similar functionality on the same biochemical targets.

As shown in FIG. 2B, a slightly more elaborate methodology includes training ML module 50' to predict efficacy of treatment further based on Drug-Target Interaction (DTI) information 30. Such DTI data 30 may include representation of an effect that a first group of drugs have on one or more biochemical targets, in an effort to deduce an effect that that another drug of interest may have on biochemical targets 50B' involved in pathogenesis of the predetermined medical condition.

The currently available methodologies presented in FIGS. 2A and 2B suffer numerous disadvantages. For example, structural data 20 should be standardized, and limited in size order to be utilized by classification model 50', and therefore may not completely, and reliably represent all aspects of large molecular structures.

In another example, classification model 50' is limited to predict an effect of a substance of interest on a specific target, and therefore is limited in scope, and cannot be easily scaled.

In another example, the empirical analysis 60' of effect on biochemical targets 50B' in effort to predict efficacy of treatment may rely on a large number of implicit and latent factors, and may therefore prove to be inaccurate in relation to specific malignancies.

In another example, available DTI data 30 is by nature very sparse: the effect that a specific substance of interest has on target molecules or pathways is typically limited to a very small group of biochemical targets.

Therefore, a need is felt for a scalable and reliable method to predict efficacy of a substance of interest in treating a predetermined malignancy.

As shown herein, embodiments of the invention may make use of (i) Drug-Drug Interaction (DDI) information, and (ii) approved drug designations, to directly predict efficacy of a substance of interest in treatment of a predetermined malignancy.

It may be appreciated that DDI information may be dense (e.g., much denser than DTI information), in a sense that drugs that are available for public consumption may be readily reported in cases of interactions with other drugs or substances.

It may also be appreciated that DDI data may include implicit, or latent information regarding the functionality of involved drugs. Such latent information is not utilized by currently available systems for predicting drug efficacy, and may provide significant improvement in this effort, as elaborated herein.

Additionally, by using approved drug designations as annotations, embodiments of the invention may use the input DDI information to directly predict drug efficacy in treatment of predetermined malignancy, and may not be limited by the understanding the contribution of specific biochemical targets in the process of pathogenesis, thereby gaining both accuracy in prediction and scalability.

Figure 3A:
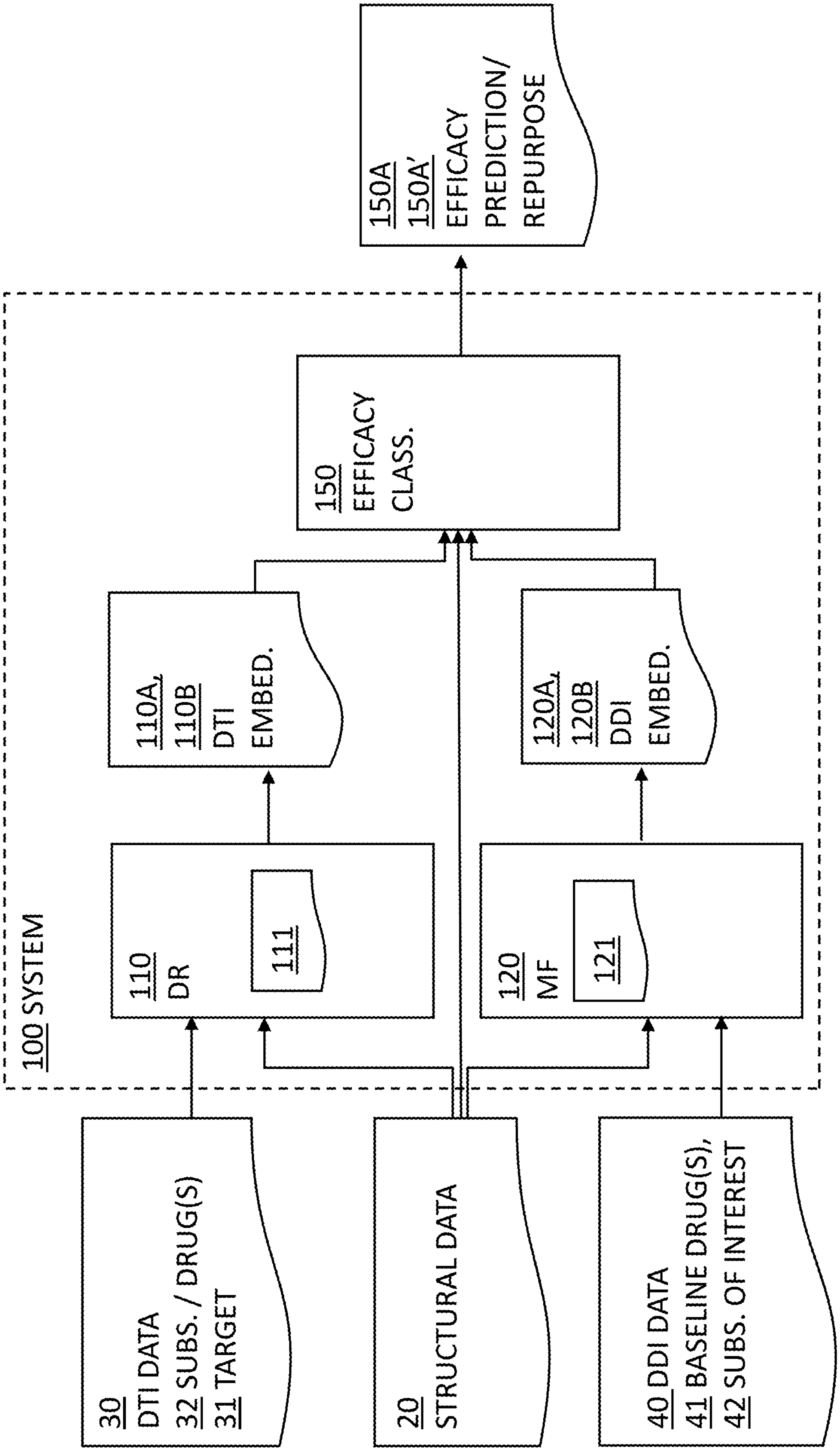
FIG. 3A is a block diagram, depicting inference of a system for predicting efficacy of drug treatment, according to some embodiments of the invention.

Reference is now made to FIG. 3A, which depicts inference of a system 100 for predicting efficacy of drug treatment, according to some embodiments of the invention.

According to some embodiments of the invention, system 100 may be implemented as a software module, a hardware module, or any combination thereof. For example, system may be, or may include a computing device such as element 1 of FIG. 1, and may be adapted to execute one or more modules of executable code (e.g., element 5 of FIG. 1) to predict efficacy of drug treatment, as further described herein.

As shown in FIG. 3A, arrows may represent a flow of one or more data elements to and/or from system 100 and/or among modules or elements of system 100. Some arrows have been omitted in FIG. 3 for the purpose of clarity.

As shown in FIG. 3A, system 100 may receive (e.g., via input device 7 of FIG. 1) a DDI data structure 40, such as a DDI tensor or matrix 40, that defines known DDIs among a plurality of drugs or substances.

For example, DDI data structure 40 may include a matrix having a plurality of entries, wherein each entry (i,j) represents a known DDI between a first substance (i) and a second substance (j) of a plurality of substances.

Entries (i,j) of DDI data structure 40 may, for example be binary (e.g., 0/1), signifying whether any DDI is known to occur between the relevant drugs or substances (i) and (j). Additionally, or alternatively, entries (i,j) may include numeric values that encode, or identify a likelihood, or severity of interaction (e.g., where a higher value represents more likely, and/or more severe DDIs). Additionally, or alternatively, entries (i,j) may include numerical or string values that encode a type of DDI (e.g., where 'A' represents an increased effect of a drugs, 'B' represents a reduced effect of a drug, etc.). Additionally, or alternatively, entries (i,j) may include numerical or string values that encode an effect of the underlying DDI (e.g., where 'K' represents Kidney damage, 'L' represents Liver damage, and the like). Other such encodings and data representations are also possible, to facilitate an underlying application of system 100.

The plurality of substances represented by, or included in DDI data structure 40 may include known drugs, that are approved for administration by a governmental authority such as the American Food and Drug Administration (FDA) for treatment of specific malignancies. This plurality of drugs may be referred to herein as "baseline drugs" 41, in a sense that other drugs or substances of interest 42 may be evaluated or analyzed in view of, or based on the relations among the plurality of baseline drugs 41.

Additionally, the plurality of substances represented by, or included in DDI data structure 40 may include one or more new, incoming substances of interest 42, for which system 100 may predict or determine efficacy in treatment of a predefined malignancy 150A.

In another example, the one or more substances of interest may include baseline drugs 41 that are approved for administration (e.g., by the FDA) for treatment of a first disease, but not cleared or not approved for treatment of a second disease of interest. In other words, system 100 may utilize DDI data structure 40 to produce a repurposing data element 150A'. Repurposing data element 150A' may include a recommendation for repurposing a substance of interest 42 that may be considered a baseline drug in relation to a first designated malignancy (e.g., initially approved by the FDA for treatment of a first disease), so as to treat a second, not-yet designated disease of interest.

As known in the art, Matrix Factorization (MF) techniques are widely used for associating a first data element, of a first group of data elements to a second data element of a second group of data elements. This association is based on representing relations between members in the first group, and members of the second group, in a low-dimensional, embedding space.

A common example of utilization of MF techniques is in recommender systems, e.g., for associating (e.g., recommending) a member of a first group (e.g., a film, from a group of films) to a member of a second group (e.g., a viewer, of a group of viewer). Pertaining to this example, each member of the first group (e.g., films) may be represented by, or attributed an embedding vector that represents its association to members of the second group (e.g., age and gender of viewers who had selected to view that film). Additionally, or alternatively, each member of the second group (e.g., a viewer) may be represented by, or attributed an embedding vector that represents its association to members of the first group (e.g., genre, and participants of films which that viewer has selected to watch).

As known in the art, the term "embedding" may be used herein in a sense of compressed, or reduced dimensionality, in relation to a vector space that represents the original dataset. In the example of film recommendation, an embedding vector representing a film may include substantially less elements than the number of viewers in the dataset, and may indicate implicit or latent qualities of the viewers who chose to watch that film. In a complementary manner, an embedding vector representing a viewer may include substantially less elements than the number of films in the dataset, and may indicate implicit or latent qualities of the films that viewer chose to watch.

According to some embodiments, system 100 may include a first embedding module, denoted herein as Matrix Factorization (MF) module 120. MF module 120 may be configured to apply an embedding function (e.g., a matrix factorization function) on the DDI data structure, to extract a DDI embedding vector 120A for at least one substance of interest 42 that is represented by DDI data structure 40.

For example, an interim vector 121 corresponding to, or representing a specific substance of interest 42 in DDI data structure 40 may include a plurality of entries, each relating to a specific drug (e.g., baseline drug 41) that is included in, or represented by DDI data structure 40. Each entry of the interim vector may include an indication of DDI (e.g., existence, severity and/or inexistence thereof) between the substance of interest 42 and a specific baseline drug 41. MF module 120 may apply an embedding function (e.g., MF function) on the interim vectors 121, to calculate a DDI embedding vector 120A. In other words, DDI embedding vector 120A may represent known DDIs between the substance of interest 42 and other baseline drugs 41 of the plurality of baseline drugs, in an embedding space, also referred to herein as a DDI embedding space.

Additionally, or alternatively, MF module 120 may calculate a DDI embedding value 120B of the substance of interest 42 based on DDI embedding vector 120A. For example, DDI embedding value 120B may be a vector that is equal to DDI embedding vector 120A. In another example, DDI embedding value 120B may include a version of DDI embedding vector 120A that is adapted, or normalized according to a predefined characteristic or quantity of the baseline drugs of DDI data structure 40.

According to some embodiments, system 100 may receive (e.g., via input device 7 of FIG. 1) a chemical structure data element 20, representing a chemical structure of a substance of interest. For example, chemical structure data element 20 may be, or may include a line-notation description of the substance of interest, such as the currently available Simplified Molecular-Input Line-Entry System (SMILES) notification.

As elaborated herein, MF module 120 may apply an embedding function on vectors of DDI data structure 40 (e.g., interim vectors 121), to calculate DDI embedding value 120B, where DDI embedding value 120B may represent information pertaining to occurrence of DDIs between a substance of interest 42 and one or more drugs 41 (e.g., baseline drugs 41 in DDI data structure 40), in a DDI embedding space.

Additionally, or alternatively, MF module may apply an embedding function on (i) interim vector 121 of a specific substance of interest 42 and (ii) chemical structure data element 20 of the specific substance of interest 42, to calculate DDI embedding value 120B. In such embodiments, DDI embedding value 120B may represent (i) information pertaining to occurrence of DDIs between a substance of interest 42 and one or more drugs 41, and (ii) information pertaining to chemical structure of the specific substance of interest 42.

According to some embodiments, system 100 may include a machine-learning (ML)-based model 150, also referred to herein as ML model 150 and efficacy classifier 150. Efficacy classifier 150 may be pretrained, as elaborated herein (e.g., in relation to FIG. 3B), to predict efficacy of the substance of interest 42 in treatment of the predetermined medical condition (e.g., a specific type of cancer), based on (i) the DDI embedding value 120B of the substance of interest 42, and (ii) the structure data element 20 of the substance of interest 42.

For example, as shown in FIG. 3A, during an inference stage system 100 may apply or infer classifier 150 on DDI embedding value 120B, and structure data element 20 of the substance of interest 42, to produce a classification output 150A. System 100 may then provide output 150A of the ML model 150 (efficacy classifier 150), e.g., via output device 8 of FIG. 1, as prediction of efficacy of the substance of interest 42 in treatment of the predetermined medical condition.

As shown in FIG. 3A, system 100 may receive (e.g., via input device 7 of FIG. 1) a DTI data structure 30, such as a DTI tensor or matrix 30, that defines known DTIs among a plurality of drugs or substances.

For example, DTI data structure 30 may include a matrix having a plurality of entries, wherein each entry (i,j) represents a known DTI between a specific drug or substance (i) of a plurality of drugs or substances 32 and a specific biochemical target 31 (j) of a plurality of biochemical targets.

The plurality of drugs or substances 32 represented by, or included in DTI data structure 30 may be, or may include the same drugs (e.g., baseline drugs) 41 and/or substances of interest 42 as represented by, or included in DDI data structure 40.

The plurality of biochemical targets 31 represented by, or included in DTI data structure 30 may each represent, or include a specific biochemical target, such as a biochemical pathway of interest, a specific type of cell of interest, a specific tissue of interest, a specific type of organism or microorganism of interest, and the like.

As known in the art, dimensionality-reduction algorithms such as Principal Component Analysis (PCA) are methods often used to reduce the dimensionality of large data sets, by transforming a large set of variables into a smaller one that still contains most of the information of the original, large data set.

According to some embodiments, system 100 may include a second embedding module 110, also denoted herein as Dimensionality Reduction (DR) module 110. DR module 110 may be configured to apply an embedding function (e.g., a PCA function) on DTI data structure 30, to extract a DTI embedding vector 110A for at least one substance of interest 32 that is included in, or represented by DTI data structure 30. A DTI embedding vector 110A of a specific substance of interest 32 may represent known DTIs between that substance of interest 32 and the plurality of biochemical targets 31, in a compressed, DTI embedding space.

Additionally, or alternatively, DR module 110 may calculate a DTI embedding value 110B of the substance of interest 32, based on DTI embedding vector 110A. For example, DTI embedding value 110B may be a vector that is equal to DTI embedding vector 110A. In another example, DTI embedding value 110B may include a version of DTI embedding vector 110A that is adapted, or normalized according to a predefined characteristic or quantity of the baseline drugs included in DTI data structure 30.

For example, an interim vector 111 corresponding to, or representing a specific substance of interest 32 in DTI data structure 30 may include a plurality of entries, each relating to a specific biochemical target 31 that is included in, or represented by DTI data structure 30.

Each entry of interim vector 111 may include an indication of DTI, such as an effect that substance of interest 32 may have on a biochemical target 31, such as a change in concentration of a specific target molecule, inhibition of a specific biochemical process or pathway, enhancement of a specific biochemical process or pathway, and the like. For example, entries (i,j) of DTI data structure 30 (and subsequent interim vector 111) may be binary, e.g., where '0' indicating no effect of substance (i) on biochemical target (j), and '1' indicating and extant effect of substance (i) on biochemical target (j). Additionally, or alternatively, entries (i,j) of DTI data structure 30 (and subsequent interim vector 111) may encode a type of effect of substance (i) on biochemical target (j), e.g., where '1' indicates inhibition of substance (i) on biochemical target (j), '2' indicates activation of biochemical target (j) by substance (i), '3' indicates potentiation of biochemical target (j) by substance (i), and the like.

DR module 110 may apply an embedding function (e.g., PCA function) on interim vectors 111, to calculate a DTI embedding vector 110A. In other words, DTI embedding vector 110A may represent known DTIs between the substance of interest 32 and biochemical targets 31 of the plurality biochemical target 31, in an embedding space, also referred to herein as a DTI embedding space.

Additionally, or alternatively, DR module 110 may apply an embedding function (e.g., a PCA function) on (i) interim vector 111 of a specific substance of interest 32 and (ii) chemical structure data element 20 of the specific substance of interest 32, to calculate DTI embedding value 110B. In such embodiments, DTI embedding value 110B may represent (i) information pertaining to DTIs between a substance of interest 32 and one or more biochemical targets 31, and (ii) information pertaining to chemical structure of the specific substance of interest 32.

According to some embodiments, ML model (efficacy classifier) 150 may be configured to receive, from DR module 110 a DTI embedding value 110B, which—as elaborated herein—may represent occurrence of DTIs between the substance of interest (32/42) and one or more biochemical targets 31 of the plurality of biochemical targets, in a DTI embedding space. ML model may be configured to predict efficacy of the substance of interest in treatment of the predetermined medical condition further based on the DTI embedding value 110B.

In other words, during an inference stage, system 100 may apply, or infer ML model (efficacy classifier) 150 on (i) DDI embedding value 120B, (ii) structure data element 20, and (iii) DTI embedding value 110B to output a prediction of efficacy 150A of a substance of interest, in treatment of a predefined malignancy.

System 100 may subsequently provide output 150A of ML model 150 as the prediction of efficacy of the substance of interest in treatment of the predetermined medical condition, e.g., via output device 8 of FIG. 1.

Figure 3B:
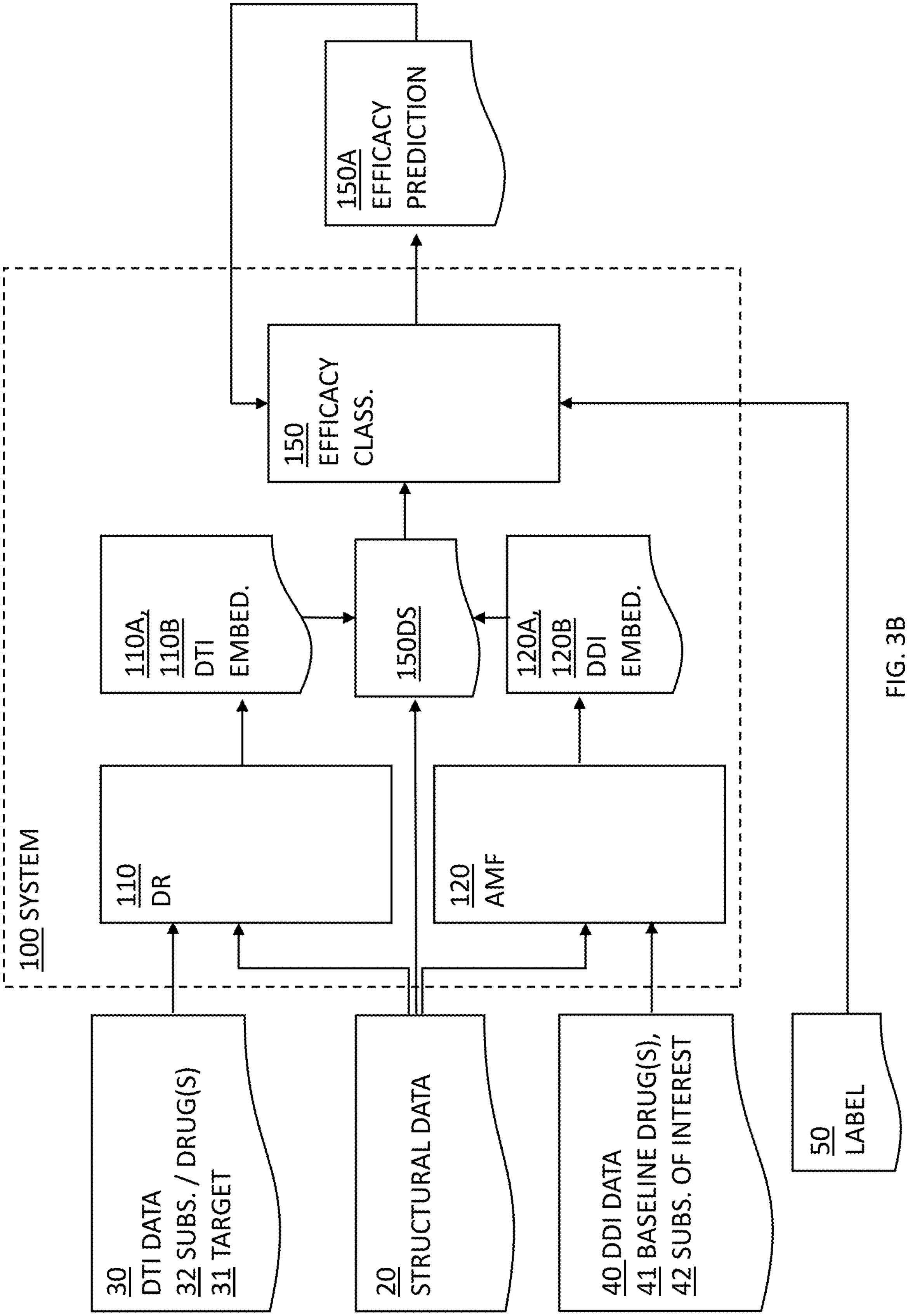
FIG. 3B is a block diagram, depicting training of a system for predicting efficacy of drug treatment, according to some embodiments of the invention.

Reference is now made to FIG. 3B, which depicts a process of training of a system 100 for predicting efficacy of drug treatment 150A, according to some embodiments of the invention.

As shown in FIG. 3B, during a training stage, ML model 150 may receive a training dataset 150DS pertaining to one or more baseline drugs 41 (32). The training dataset 150DS may include, for example one or more DTI embedding vectors 110A and/or DTI embedding values 110B respective of the one or more baseline drugs 41 (32). Additionally, or alternatively, the training dataset 150DS may include one or more DDI embedding vectors 120A and/or DDI embedding values 120B respective of the one or more baseline drugs 41 (32). Additionally, or alternatively, the training dataset 150DS may include one or more structural data elements 20 respective of the one or more baseline drugs 41 (32).

Additionally, or alternatively, ML model 150 may receive one or more label data elements 50, pertaining to the one or more first baseline drugs 41 (32). According to some embodiments, each label 50 may include an annotation having a trinary value, where a value of '1' indicates that the respective baseline drug is approved or designated (e.g., by the FDA) for use as treatment for the predetermined medical condition (the malignancy of interest), '0' indicates that the respective baseline drug is not approved or designated for use as treatment for the predetermined medical condition, and another (e.g., "don't-care") value indicates that the respective baseline drug is currently undergoing a process of approval (e.g., clinical trials) for designation of treatment for the predetermined medical condition.

According to some embodiments, during the training stage, system 100 may use the one or more label data elements 150 as supervisory data, to train ML based model 150, to predict efficacy 150A of a target drug 41 or substance of interest 42 in treatment of the predetermined medical condition.

For example, ML model 150 may be implemented by a multi-layered, interconnected neural network architecture, where each edge of the neural network is associated by a configurable weight value. During training, system 100 may receive predicted efficacy 150A of a specific target drug 41 or target substance of interest 42 as feedback, and apply a learning algorithm (e.g., a back-propagation algorithm), to modify weights of ML model 150. The learning algorithm may be configured to minimize an error or difference between the outcome of ML model 150 (e.g., predicted efficacy value 150A of target substance of interest 42) and ground-truth data as represented by label 50 (e.g., actual designation by the FDA of target substance of interest 42 for treatment of the disease of interest).

In other words, during a training stage, ML model 150 may receive a training dataset 150DS that may include (i) one or more first DDI embedding values 120B, corresponding to one or more respective, first baseline drugs 41 (32), (ii) one or more first DTI embedding values 110B, corresponding to the one or more respective, first baseline drugs 41 (32), and/or (iii) one or more first structure data elements 20, corresponding to the one or more respective, first baseline drugs 41 (32). Additionally, or alternatively, ML model 150 may receive one or more label data elements 50, corresponding to the one or more respective, first baseline drugs 41 (32), where each label 50 annotates whether the respective baseline drug is approved for use as a remedy for the predetermined medical condition, or not.

System 100 may use the one or more label data elements as supervisory data, to train the ML based model 150 to predict efficacy of the one or more first baseline drugs 41 (32) in treatment of the predetermined medical condition, based on the one or more first DDI embedding values 120B, the one or more first DTI embedding values 110B, and/or one or more first structure data elements 20.

In a subsequent inference stage, system 100 may receive a second DDI embedding value 120B, a second DTI embedding value 110B, and/or a second structure data element 20, corresponding to a target substance of interest 42. As known in the art, system 100 may utilize the pretraining of ML model 150 to provide the required classification output. Pertaining to embodiments of this invention, system 100 may utilize the pretraining of ML model 150 to predict efficacy of treatment of target substance of interest 42, according to the second DDI embedding value 120B, second DTI embedding value 110B and/or second structure data element 20, based on the training of ML model 150.

Reference is now made to FIG. 4, which is a table elaborating an exemplary comparison between different methods of drug treatment efficacy prediction.

As elaborated herein, currently available systems may employ molecular structure similarity metrics and/or DTI data among drugs, to evaluate effect on biochemical targets.

In the example depicted in FIG. 4, embodiments of the invention further used FDA label data 50, to predict drug treatment efficacy, in relation to four datasets:

In the first and second lines, molecular structure similarity metrics were used with, and without DTI data, respectively, to predict drug treatment efficacy. This resulted in Receiver Operating Characteristic (ROC) Area Under Curve (AUC) of 0.806 and 0.853 respectively.

When provided with DDI data, the AUC was significantly improved to 0.897 and 0.909, as shown in the third and fourth lines respectively. It may therefore be argued that DDI data, which is utilized by embodiments of the invention, may include latent information that is helpful for correctly predicting drug treatment efficacy.

Figure 5:
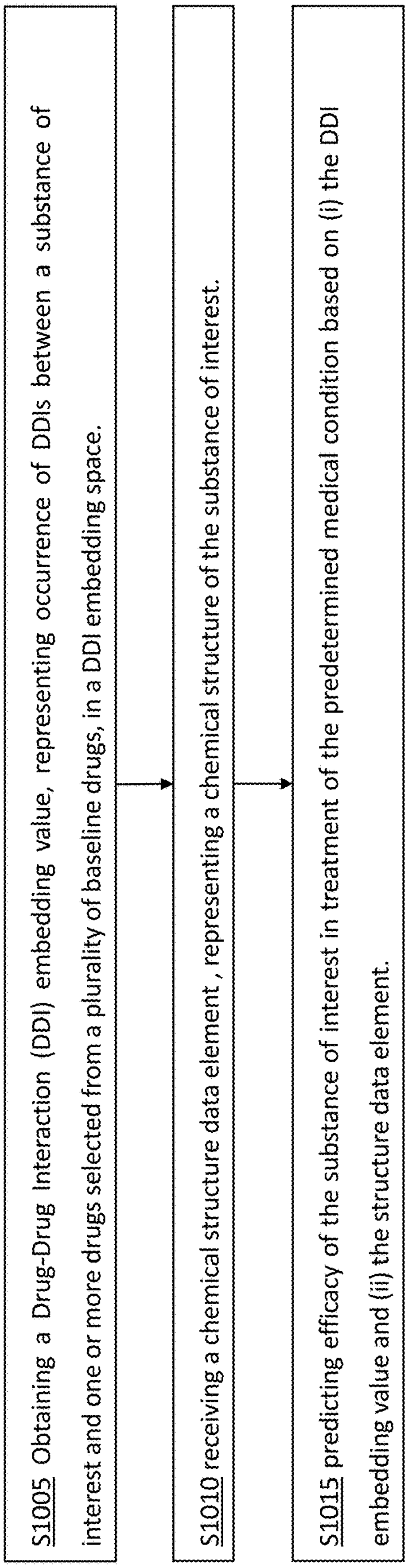
FIG. 5 is a flow diagram, depicting a method of predicting efficacy of drug treatment, according to some embodiments of the invention.

Reference is now made to FIG. 5, which is a flow diagram depicting a method of predicting efficacy of drug treatment by at least one processor (e.g., processor 2 of FIG. 1), according to some embodiments of the invention.

As elaborated herein (e.g., in relation to FIG. 3A), and shown in step S1005, processor 2 may obtain (e.g., via MF module of FIG. 3A) a DDI embedding value, representing occurrence of DDIs between a substance of interest and one or more drugs selected from a plurality of baseline drugs, in a DDI embedding space.

As shown in step S1010, processor 2 may receive (e.g., via input device 7 of FIG. 1) a chemical structure data element (e.g., a SMILES data element), representing a chemical structure of the substance of interest.

As shown in step S1015, processor 2 may employ a machine learning model (e.g., ML 150) to predict efficacy of the substance of interest in treatment of the predetermined medical condition or malignancy, based on (i) the DDI embedding value and (ii) the structure data element.

Embodiments of the invention include a practical application for predicting, or highlighting efficacy of drugs or substances of interest, for treating a predetermined disease. Such application may allow for example, a repurposing of a drug, that has been officially approved by proper authorities (e.g., the FDA) for treatment of a first disease, as a treatment for a second, possibly unrelated disease. It may be appreciated that such identification of commercially available, previously approved drugs for treatment of new malignancies may reduce developmental efforts and costs significantly, and expediate treatment of such malignancies, for the benefit of the population.

Embodiments of the invention are therefore firmly embedded in the technological fields of drug development and assistive diagnosis. As elaborated herein, embodiments of the invention may include several improvements over currently available technology of drug development:

For example, and as elaborated herein, system 100 may utilize available DDI data, to extract latent information that is predictive in relation to drug efficacy. In another example, system 100 may utilize available labeling, indicating whether specific baseline drugs are approved or designated (e.g., by the FDA) for use as treatment for the predetermined medical condition (e.g., the malignancy of interest). As explained herein, (e.g., in relation to FIG. 4) usage of this information has been experimentally shown to contribute greatly to the accuracy of prediction of a substance of interest, such as Eravacycline, which is a registered antibacterial drug, for treatment of pancreatic cancer.

Unless explicitly stated, the method embodiments described herein are not constrained to a particular order or sequence. Furthermore, all formulas described herein are intended as examples only and other or different formulas may be used. Additionally, some of the described method embodiments or elements thereof may occur or be performed at the same point in time.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

Various embodiments have been presented. Each of these embodiments may of course include features from other embodiments presented, and embodiments not specifically described may include various features described herein.

Additional aspects of the invention are provided in Appendix 1.

The invention claimed is:

1. A method of predicting efficacy of treatment of a predetermined medical condition by at least one processor, the method comprising:

receiving a Drug-Drug Interaction (DDI) data structure that defines known DDIs among a plurality of drugs, wherein the plurality of drugs comprises a substance of interest and a plurality of baseline drugs, in a DDI embedding space;

receiving a chemical structure data element, representing a chemical structure of the substance of interest;

applying an embedding function on the DDI data structure, to extract a DDI embedding vector for the substance of interest, wherein the DDI embedding vector represents known DDIs between the substance of interest and the plurality of baseline drugs, in the DDI embedding space;

calculating a DDI embedding value of the substance of interest based on the DDI embedding vector;

applying a machine-learning (ML)-based model on (i) the DDI embedding value and (ii) the chemical structure data element, to predict efficacy of the substance of interest in treatment of the predetermined medical condition; and generating a repurposing recommendation for the substance of interest to treat the predetermined medical condition, wherein the substance of interest is not approved for treatment of the predetermined medical condition.

2. The method of claim 1, further comprising:

obtaining a Drug-Target Interaction (DTI) embedding value, representing occurrence of DTIs between the substance of interest and one or more biochemical targets selected from a plurality of biochemical targets, in a DTI embedding space; and predicting efficacy of the substance of interest in treatment of the predetermined medical condition further based on the DTI embedding value.

3. The method of claim 2, wherein predicting efficacy of the substance of interest comprises:

applying the ML-based model on (i) the DDI embedding value, (ii) the chemical structure data element, and (iii) the DTI embedding value; and providing an output of the first ML model as the prediction of efficacy of the substance of interest in treatment of the predetermined medical condition.

4. The method of claim 2, wherein obtaining a DTI embedding value comprises:

receiving a DTI data structure comprising a plurality of entries, wherein each entry (i,j) represents a known DTI between a specific substance (i) of a plurality of substances and a specific biochemical target (j) of a plurality of biochemical targets, wherein said plurality of substances comprises the plurality of baseline drugs and the substance of interest;

applying an embedding function on the DTI data structure, to extract a DTI embedding vector, representing known DTIs between the substance of interest and the plurality of biochemical targets, in the DTI embedding space; and calculating the DTI embedding value of the substance of interest based on the DTI embedding vector.

5. The method of claim 1, wherein the chemical structure data element is a line-notation description of the substance of interest.

6. The method of claim 1, wherein the DDI data structure comprises a plurality of entries, wherein each entry (i,j) represents a known DDI between a first substance (i) and a second substance (j) of a plurality of substances, wherein said plurality of substances comprises the plurality of baseline drugs and the substance of interest.

7. The method of claim 1, wherein training the first-ML based model comprises:

receiving a training dataset pertaining to one or more first baseline drugs;

receiving one or more label data elements, pertaining to the one or more first baseline drugs, wherein each label annotates whether the respective baseline drug is approved for use as a remedy for the predetermined medical condition; and using the one or more label data elements as supervisory data, to train the ML based model, to predict efficacy of a target substance of interest in treatment of the predetermined medical condition.

8. The method of claim 1, wherein training the ML based model comprises:

receiving a training dataset comprising: (i) one or more first DDI embedding values, corresponding to one or more respective, first baseline drugs, and (ii) one or more first chemical structure data elements, corresponding to the one or more respective, first baseline drugs;

receiving one or more label data elements, corresponding to the one or more respective, first baseline drugs, wherein each label annotates whether the respective baseline drug is approved for use as a remedy for the predetermined medical condition; and using the one or more label data elements as supervisory data, to train the first ML based model, to predict efficacy of the one or more first baseline drugs in treatment of the predetermined medical condition, based on the one or more first DDI embedding values and one or more first chemical structure data elements.

9. The method of claim 8, further comprising, during an inference stage:

receiving a second DDI embedding value and a second chemical structure data element, corresponding to a target substance of interest; and predicting efficacy of treatment of that target substance of interest, according to the second DDI embedding value and second structure data element, based on said training.

10. The method of claim 1, wherein training the first ML based model comprises:

receiving a training dataset comprising: (i) one or more first DDI embedding values, corresponding to one or more respective, first baseline drugs, (ii) one or more first DTI embedding values, corresponding to the one or more respective, first baseline drugs, and (iii) one or more first chemical structure data elements, corresponding to the one or more respective, first baseline drugs;

receiving one or more label data elements, corresponding to the one or more respective, first baseline drugs, wherein each label annotates whether the respective baseline drug is approved for use as a remedy for the predetermined medical condition, or not; and using the one or more label data elements as supervisory data, to train the first ML based model, to predict efficacy of the one or more first baseline drugs in treatment of the predetermined medical condition, based on the one or more first DDI embedding values, the one or more first DTI embedding values, and one or more first chemical structure data elements.

11. The method of claim 10, further comprising, during an inference stage:

receiving a second DDI embedding value, a second DTI embedding value, and a second chemical structure data element, corresponding to a target substance of interest; and predicting efficacy of treatment of that target substance of interest, according to the second DDI embedding value, second DTI embedding value and second structure data element, based on said training.

12. A system for predicting efficacy of treatment of a predetermined medical condition, the system comprising: a non-transitory memory device, wherein modules of instruction code are stored, and at least one processor associated with the memory device, and configured to execute the modules of instruction code, whereupon execution of said modules of instruction code, the at least one processor is configured to:

receive a Drug-Drug Interaction (DDI) structure, that defines known DDIs among a plurality of drugs, wherein the plurality of drugs comprises a substance of interest and a plurality of baseline drugs, in a DDI embedding space;

receive a chemical structure data element, representing a chemical structure of the substance of interest;

apply an embedding function on the DDI data structure, to extract a DDI embedding vector for the substance of interest, wherein the DDI embedding vector represents known DDIs between the substance of interest and the plurality of baseline drugs, in the DDI embedding space;

apply at least one machine-learning (ML)-based model on (i) the DDI embedding value of the substance of interest and (ii) the structure data element of the substance of interest, to predict efficacy of the substance of interest in treatment of the predetermined medical condition; and generate a repurposing recommendation for the substance of interest to treat the predetermined medical condition, wherein the substance of interest is not approved for treatment of the predetermined medical condition.

13. The system of claim 12, wherein the at least one processor is further configured to:

obtain a Drug-Target Interaction (DTI) embedding value, representing occurrence of DTIs between the substance of interest and one or more biochemical targets selected from a plurality of biochemical targets, in a DTI embedding space; and predict efficacy of the substance of interest in treatment of the predetermined medical condition further based on the DTI embedding value.

14. The system of claim 13, wherein the at least one processor is configured to predict efficacy of the substance of interest by:

applying the at least one ML-based model on (i) the DDI embedding value, (ii) the structure data element, and (iii) the DTI embedding value; and providing an output of the at least one ML model as the prediction of efficacy of the substance of interest in treatment of the predetermined medical condition.

15. The system of claim 13, wherein the at least one processor is configured to obtain a DTI embedding value by:

receiving a DTI data structure comprising a plurality of entries, wherein each entry (i,j) represents a known DTI between a specific substance (i) of a plurality of substances and a specific biochemical target (j) of a plurality of biochemical targets, wherein said plurality of substances comprises the plurality of baseline drugs and the substance of interest;

applying an embedding function on the DTI data structure, to extract a DTI embedding vector, representing known DTIs between the substance of interest and the plurality of biochemical targets, in the DTI embedding space; and calculating the DTI embedding value of the substance of interest based on the DTI embedding vector.

16. The system of claim 12, wherein the chemical structure data element is a line-notation description of the substance of interest.

17. The system of claim 12, wherein the DDI data structure comprises a plurality of entries, wherein each entry (i,j) represents a known DDI between a first substance (i) and a second substance (j) of a plurality of substances, wherein said plurality of substances comprises the plurality of baseline drugs and the substance of interest.

18. The system of claim 12, wherein the at least one processor is configured to train the first ML based model by:

receiving a training dataset pertaining to one or more first baseline drugs;

receiving one or more label data elements, pertaining to the one or more first baseline drugs, wherein each label annotates whether the respective baseline drug is approved for use as a remedy for the predetermined medical condition; and using the one or more label data elements as supervisory data, to train the first ML based model, to predict efficacy of a target substance of interest in treatment of the predetermined medical condition.

* * * * *